(12) United States Patent
Lucassen et al.

(10) Patent No.: US 9,498,136 B2
(45) Date of Patent: Nov. 22, 2016

(54) CLASSIFICATION OF TUMOR TISSUE WITH A PERSONALIZED THRESHOLD

(75) Inventors: Gerhardus Wilhelmus Lucassen, Eindhoven (NL); Bernardus Hendrikus Wilhelmus Hendriks, Eindhoven (NL); Rami Nachabe, Eindhoven (NL)

(73) Assignee: Koninklijke Philips N.V, Eindhoven (NL)

( * ) Notice: Subject to any disclaimer, the term of this patent is extended or adjusted under 35 U.S.C. 154(b) by 121 days.

(21) Appl. No.: 14/112,555

(22) PCT Filed: Apr. 10, 2012

(86) PCT No.: PCT/IB2012/051742
§ 371 (c)(1),
(2), (4) Date: Oct. 18, 2013

(87) PCT Pub. No.: WO2012/143816
PCT Pub. Date: Oct. 26, 2012

(65) Prior Publication Data
US 2014/0046197 A1    Feb. 13, 2014

Related U.S. Application Data

(60) Provisional application No. 61/557,017, filed on Nov. 8, 2011.

(30) Foreign Application Priority Data

Apr. 18, 2011   (EP) ..................... 11162815

(51) Int. Cl.
*A61B 5/00* (2006.01)
*A61B 1/00* (2006.01)
*G01N 21/64* (2006.01)

(52) U.S. Cl.
CPC ............... *A61B 5/0075* (2013.01); *A61B 1/00* (2013.01); *A61B 5/0071* (2013.01);
(Continued)

(58) Field of Classification Search
CPC   A61B 5/0075; A61B 5/0084; A61B 5/0091; A61B 5/0071; A61B 5/4887; A61B 5/6848; A61B 5/6852; A61B 1/00; G01N 21/64; G01N 2021/6421
See application file for complete search history.

(56) References Cited

U.S. PATENT DOCUMENTS

| 5,006,987 A | 4/1991 | Harless |
| 5,596,992 A | 1/1997 | Haaland et al. |

(Continued)

FOREIGN PATENT DOCUMENTS

| JP | 20080221457 A | 4/2010 |
| WO | WO0118771 | 3/2001 |
| WO | 2011031738 A1 | 3/2011 |

OTHER PUBLICATIONS

J. Renwick Beattle, et al., Classification of Adipose Tissue Species Using Raman Spectroscopy; Lipids (2007) 42, pp. 679-685.

(Continued)

*Primary Examiner* — Long V Le
*Assistant Examiner* — Colin T Sakamoto

(57) ABSTRACT

The present invention deals with discrimination of malignant tissue from normal and benign tissue in a single patient on the basis of optical spectroscopic measurements. Starting from spectroscopic measurements in normal tissue, reference values are obtained for the normal class. With spectroscopic measurements in other tissues data points can be assigned to new class(es) when the spectral characteristics fall outside a threshold defining the reference class. Thresholds between different classes can also be defined. Finding (the transition to) malignant tissue is based on comparing the spectroscopic values to the classification threshold discriminating normal and benign versus malignant tissue. Thus, the basis of normal spectroscopic measurements is tuned to the individual patient characteristic. Discriminating the normal plus benign and malignant from that reference is more efficient compared to the reference of the all patient database.

20 Claims, 9 Drawing Sheets

(52) U.S. Cl.
CPC .......... *A61B 5/0084* (2013.01); *A61B 5/0091* (2013.01); *A61B 5/4887* (2013.01); *A61B 5/6848* (2013.01); *A61B 5/6852* (2013.01); *G01N 21/64* (2013.01); *G01N 2021/6421* (2013.01)

(56) References Cited

U.S. PATENT DOCUMENTS

| | | |
|---|---|---|
| 6,835,572 B1 | 12/2004 | Mountford et al. |
| 2003/0022141 A1 | 1/2003 | Packard |
| 2006/0173352 A1 | 8/2006 | Lilge et al. |
| 2006/0272652 A1 | 12/2006 | Stocker et al. |
| 2007/0167836 A1 | 7/2007 | Scepanovic et al. |
| 2008/0037922 A1 | 2/2008 | Hayashi et al. |
| 2008/0221455 A1 | 9/2008 | Marshik-Geurts et al. |
| 2008/0221457 A1 | 9/2008 | Zeng et al. |
| 2009/0002702 A1 | 1/2009 | Maier et al. |
| 2009/0317856 A1 | 12/2009 | Mycek et al. |
| 2010/0054294 A1 | 3/2010 | Yukawa |

OTHER PUBLICATIONS

D.M. Haaland, et al., Partial Least-Squares Methods for Spectral Analyses. 2; Application to Simulated and Glass Spectral Data, Sandia National Laboratories, Albuquerque NW, Analytical Chemistry, vol. 60, No. 11, Jun. 1, 1988, pp. 1202-1208.

R. Nachabe, et al., "Estimation of Biological Chromophores Using Diffuse Optical Spectroscopy: Benefit of Extending the UV-VIS Wavelength Range to Include 1000 to 1600 nm", Optics Express vol. 18, No. 24 (2010).

K.S. Booksh, "Chemometric Methods in Process Analysis", Encyclopedia of Analytical Chemistry, (2000), pp. 8145-8169.

D.M. Haaland et al. "Partial Least-Squares Methods for Spectral Analyses. 1. Relation to Other Quantitative Calibration Methods and the Extraction of Qualitative Information", Sandia National Laboratories, Albuquerque, NM, Analytical Chemistry, vol. 60, No. 11, Jun. 1, 1988, pp. 1193-1202.

Skvortsova, Yulia Alexandrovna, "Simulation of tissue for biomedical applications", PhD diss., University of Iowa, 2009. http://ir.uiowa.edu/etd/436.

CLASSIFICATION OF TUMOR TISSUE WITH A PERSONALIZED THRESHOLD

CROSS-REFERENCE TO PRIOR APPLICATIONS

This application is the U.S. National Phase application under 35 U.S.C. §371 of International Application Serial No. PCT/IB2012/051742, filed on Apr. 10, 2012, which claims the benefit of U.S. Application Ser. No. 61/557,017, filed on Nov. 8, 2011 and European Application Serial No. 11162815.2, filed on Apr. 18, 2011. These applications are hereby incorporated by reference herein.

FIELD OF THE INVENTION

The invention relates to a method of and to a system for tissue discrimination on the basis of spectroscopic measurements and analysis.

BACKGROUND OF THE INVENTION

In the field of oncology it is important to be able to discriminate tumor tissue from normal tissue. Golden standard is to inspect tissue at the pathology department after a biopsy or after surgical resection. A drawback of this current way of working is that real time feedback during the procedure of taking a biopsy or performing the surgical resection is missing. Incorporating optical fibers in a biopsy needle would be for instance of great interest to physicians to use as a feedback device during their clinical interventions. Various optical methods can be employed, e.g., diffuse reflectance spectroscopy (DRS) and autofluorescence measurement as the techniques that are most commonly investigated. The spectroscopic data are used to classify the different tissue types using standard classification methods. Usually a database is built for classification with spectra from many patients and is used for regression for new measurements to predict the class to which they belong.

A problem with classifying tissue type of an individual patient using such a database is that inter-patient variance hampers tissue discrimination. It has been demonstrated that in breast tissue the fat content increases whereas glandular tissue decreases with age. Therefore, a very large standard deviation in fat and collagen exists due to a wide range of age. The sensitivity and specificity of the methods using spectroscopic point measurements are moderate (50-85%) and results strongly vary in the literature. The moderate sensitivity makes the approach not optimal for an individual patient approach.

FIG. 2 shows inter-patient variation in a score plot of partial least squares discriminant analysis (PLS-DA) prediction scores of breast tissue classification of all patients. More specifically, FIG. 2 shows a result of an all-patient PLS-DA analysis of diffuse reflectance spectroscopic measurements on ex-vivo human breast tissues samples. From FIG. 2 it can be seen that inter-patient variation is an issue when discriminating for example fibroadenoma (FA, benign) from gland (G, normal) tissue, the gland tissue represented by symbols "◊" which are scattered and mix up with other tissue type measurements. In FIG. 2, other tissue types are fibroadenoma (FA) represented by symbols "+", adenocarcinoma (A) represented by symbols "x", ductal carcinoma in situ (DCIS) represented by symbols "○", and fat (F) represented by symbols "□".

Thus, a discrimination would be desirable, which is tuned to the individual patient, where spectroscopic measurements at different positions such as in normal and/or benign and malignant tissues in the individual patient are obtained, if possible, a classification model can be provided using individual patient data and a priori spectroscopic and clinical patient knowledge, and tissue types are classified for the patient without hindrance of inter-patient variance.

However, it is in this case not trivial how to classify individual patient spectroscopic with high sensitivity and specificity. Neither is it straightforward to determine whether the data collected in the above step one is malignant tissue (chicken-egg problem). Furthermore, from the above it is not clear how this approach would fit in the workflow of a clinician. Building first a database for an individual patient and then using this for further classification is time consuming compared to using a pre-collected database of various patients and performing classification based on this database. In this case the database need not to be built up during the intervention but hampers from the above mentioned inter-patient variations which results in low sensitivity. The sensitivity and specificity of conventional methods using spectroscopic point measurements usually are moderate and also strongly vary in the literature. The moderate sensitivity makes the method not ideal for an individual patient. To overcome this problem a method is needed that is tuned to the individual patient.

The US 2006/0173352 A1 discloses a method for detecting pre-disease transformations in tissue of mammals, which comprises illuminating a volume of selected tissue with light having wavelengths covering a pre-selected spectral range, detecting light transmitted through, or reflected from, the volume of the selected tissue, and obtaining a spectrum of the detected light. The spectrum of detected light is then represented by one or more basis spectral components. The associated scalar coefficient of the each of the basis spectral components is correlated with a pre-selected property of the selected tissue known to be indicative of susceptibility of the tissue for the pre-selected disease to obtain the susceptibility for the mammal to developing the pre-selected disease. Statistical significance for principal component analysis prediction was established using high density measure (HDM) as it is preferable over increased low density measure (LDM) both are similar sensitivity and specificity.

Furthermore, the US 2009/0317856 A1 disclosed multimodal optical spectroscopy systems and methods, in which a spectroscopic event is produced to obtain spectroscopic response data from biological tissue and compare the response data with preset criteria configured to correlate the measured response data and the most probable attributes of the tissue, thus facilitating classification of the tissue based on those attributes for subsequent biopsy or remedial measures as necessary. Tissue classification algorithms were developed to employ reflectance and fluorescene spectroscopy for differentiating between human pancreatic adenocarcinoma and pancreatitis tissue. Linear Discriminant Analysis was used to classify the test data into adenocarcinoma or not adenocarcinoma based on the fit-coefficient values for all or a subset of four principal component values.

Additionally, the US 2007/0167836 A1 discloses a system for multi modal spectroscopy where Raman spectroscopy is combined with fluorescence, reluctance and optionally light scattering spectroscopy. An algorithm for diagnosis of vulnerable plaque incorporates contributions from metabolically active, potential scatterers like foam cells as well as non-metabolically active plaque constituents like the necrotic core. The key spectroscopic parameters obtained from intrinsic fluorescence signature, diffuse reflectance spectroscopy and Raman spectroscopies are categorized as yes/no results based on threshold values.

Further, the US 2008/0221455 A1 discloses methods and devices for characterizing tissue in vivo, e.g., in walls of blood vessels, to determine whether the tissue is healthy or diseased. Results are displayed with or without thresholds. A single threshold may not be optimal for all patients because of inter-patient variation. In other words, the reflected radiation in one patient may not mean the same thing in another patient. Displaying the data directly enables the operator to decide upon a patient-specific threshold after taking individual patient considerations into account.

Moreover, the US 2009/0002702 A1 discloses a system to provide a diagnosis of the renal disease state of a test renal sample. A database containing a plurality of reference Raman data sets is provided where each reference Raman data set has an associated known renal sample and an associated known renal disease state. A test renal sample is irradiated with substantially monochromatic light to generate scatted photons resulting in a test Raman data set. The test Raman data set is compared to the plurality of reference Raman data sets using a chemometric technique. Based on the comparison, a diagnosis of a renal disease state of the test renal sample is provided and the data set is classified into predetermined cases.

Finally, the US 2008/0221457 A1 discloses methods and apparatus for classifying tissue use features of Raman spectra and background fluorescent spectra. The spectra may be acquired in the near-infrared wavelengths. Principal component analysis and linear discriminant analysis of reference spectra may be used to obtain a classification function that accepts features of the Raman and background fluorescence spectra for test tissue and yields an indication as to the likelihood that the test tissue is abnormal. The methods and apparatus may be applied to screening for skin cancers or other diseases. Difference as well us ine peak positions and bandwidths of the two melanin Raman bands may be included as features and used for non-invasive melanoma detection.

SUMMARY OF THE INVENTION

It is an object of the present invention to provide an improved method and system for discriminating malignant tissue and benign tissue from normal tissue in an individual patient.

The object is achieved by a system and a method as claimed herein.

Accordingly, optical spectra are acquired from a position inside the body and processed so as to discriminate tissue based on a procedure where data of a first tissue type class is collected (e.g. normal tissue) using at least one classification threshold which is defined relative to this first tissue type class. It is thus assured on the basis of the image guidance that the measurement relates to normal tissue. The center of gravity of the reference measurements is based on the actual individual patient, while in conventional systems this is based on the many-patient database. The basis of normal spectroscopic measurements can thus be tuned to the individual patient characteristic. Discriminating the normal plus benign and malignant from that reference is more efficient compared to the reference of the all patient database.

In more detail, the procedure to obtain the threshold for different tissue type classes (e.g. normal, benign and malignant tissue types) includes obtaining spectroscopic measurements by means of a device like a needle, preferably at several different positions, e.g. in normal tissue of the patient using image guidance and/or the experience of the physician as a starting point. The spectral absorption and scattering characteristics or fluorescence characteristics derived from fits (e.g. on hemoglobin, fat, beta carotene, bilirubin, water content and amount of scattering) of these reference measurements define these data points to form a first tissue type class. The a priori knowledge on the spectral characteristics of a reference tissue is used to define a threshold for the cloud of data points that belong to this reference set. Then, the needle or other interventional device (e.g. catheter or endoscope or the like) is used to obtain spectroscopic data from other tissue positions. When these spectral characteristics fall outside the above threshold, a second tissue type class is defined. These measured tissue positions could be suspicious, and in a practical situation the physician could based on the spectral information decide to take a biopsy.

According to a first aspect, the predetermined spectral characteristics may comprise absorption and scattering characteristics, or fluorescence characteristics.

According to a second aspect which can be combined with the above first aspect, the console may be arranged for recognizing data points of the second tissue type class from the shape of a plot of data points. Thus, the discrimination may be based on a clustering approach which allows easy and simple detection.

According to a third aspect which can be combined with the above first or second aspect, the first tissue type class may relate to fat or gland tissue and the second tissue type class relates to adenocarcinoma or ductal carcinoma in situ tissue. Thereby, discrimination of carcinoma-type of tissue can be improved by the proposed personalized or individualized approach. However, any type of tissue can be discriminated, such as different normal types of tissue, or normal and diseased tissue, or normal and tumor tissue, or normal tissue, benign and malignant tissue.

According to a fourth aspect which can be combined with any of the above first to third aspects, the console may be arranged for defining a third tissue type class and using the orientation of a triangle defined by data points of the three tissue type classes to assign a tissue type to the second and third tissue type classes. Thus, spectral characteristics of measurements in different positions in the tissue may make up additional classes and thresholds between the classes.

According to a fifth aspect which can be combined with any of the above first to fourth aspects, the console may be arranged for using a correlation of measured spectra with a database of individual patient spectra to discriminate among the different tissue types. Thus, an alternative or additional correlation-based discrimination approach can be provided.

According to a sixth aspect which can be combined with any of the above first to fifth aspects, the console may be arranged for generating a reference map in a space defined by at least two of extracted water, lipid and collagen fractions, for classifying the space based in the tissue types, and for tagging the spectroscopic measurement on the reference map. Thus, an alternative or additional map-based discrimination approach can be provided.

Further advantageous embodiments are defined below.

BRIEF DESCRIPTION OF THE DRAWINGS

These and other aspects of the invention will be apparent from and elucidated with reference to the embodiments described hereinafter.

In the drawings.

DETAILED DESCRIPTION OF THE INVENTION

A system as used in the following embodiments performs spectroscopic measurements of tissue under investigation, The system is configured to analyze these measurements in order to determine the type of the tissue. To this end, the system may use one or more analyzing methods that are generally known in the art. Generally known methods are described for example in Chemometric Methods in Process Analysis, Karl S. Booksh in; *Encyclopedia of Analytical Chemistry*; R. A. Meyers (Ed.); pp. 8145-8169; John Wiley & Sons Ltd, Chichester, 2000, or Partial Least-Squares Methods for Spectral Analyses. 1.; Relation to Other Quantitative Calibration Methods and the Extraction of Qualitative Information; David M. Haaland* and Edward V. Thomas; *Sandia National Laboratories*, Albuquerque, N. Mex. 87185; ANALYTICAL CHEMISTRY, VOL. 60, NO. 11, Jun. 1, 1988 p 1193-1202, or Partial Least-Squares Methods for Spectral Analyses. 2.; Application to Simulated and Glass Spectral Datal; David M. Haaland* and Edward V. Thomas; Sandia National Laboratories, Albuquerque, N. Mex. 87185; ANALYTICAL CHEMISTRY, VOL. 60, NO. 11, Jun. 1, 1988, p 1202-1208.

In particular PLS-DA is described in Classification of Adipose Tissue Species using Raman Spectroscopy; J. Renwick Beattie Æ Steven E. J. Bell Æ; Claus Borggaard Æ Anna M. Fearon Æ; Bruce W. Moss Lipids (2007) 42:679-685.

The system according to the following embodiments is an improvement of the medical device consisting of a console and an optical probe as is for instance described in R. Nachabá et al., "Estimation of biological chromophores using diffuse optical spectroscopy: benefit of extending the UV-VIS wavelength range to include 1000 to 1600 nm", Biomedical Optics Express 1, 2010. Various embodiments of the method and of the system according to the invention are described in more detail below.

Figure 1:
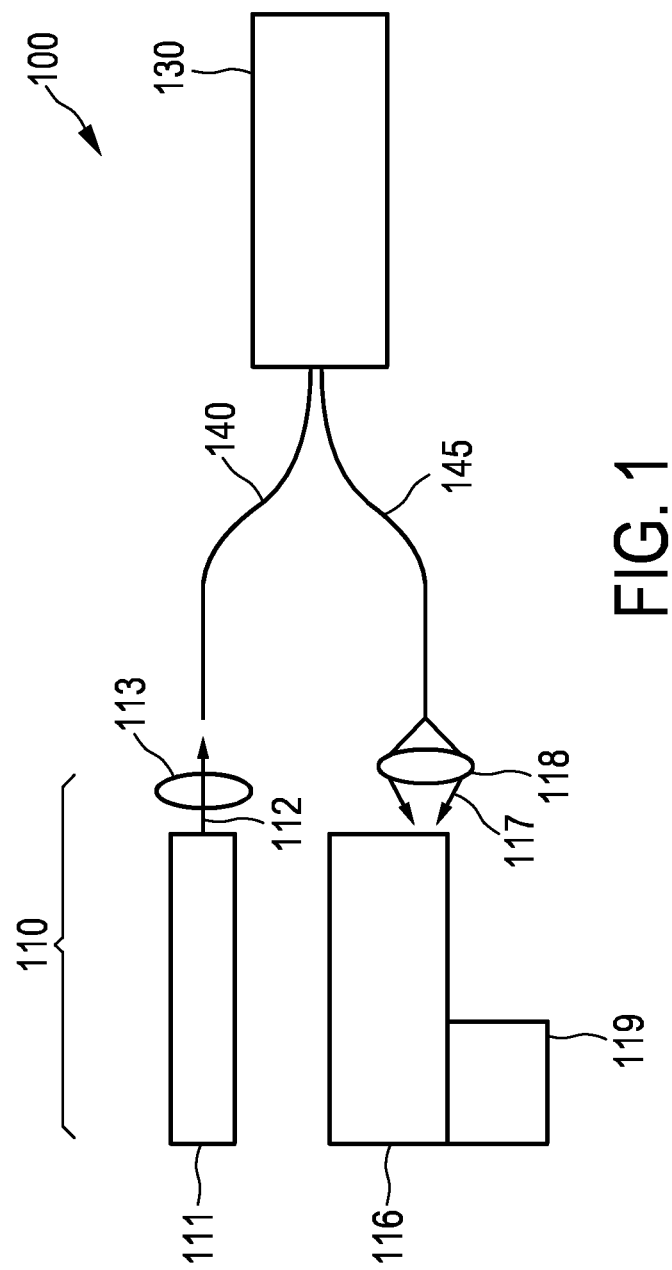
FIG. 1 shows a schematic block diagram of a medical apparatus according to various embodiments.

FIG. 1 shows a medical apparatus 100 according to various embodiments of the present invention. The medical apparatus 100 comprises an optical instrument 110 and a medical device. According to various embodiments described here the medical device is a photonic needle 130. However, it may be any other medical device or probe which allows spectroscopic tissue measurements, e.g., any optical probe or catheter-type device. The medical apparatus 100 is in particular suitable for optically investigating tissue material which may be surrounded laterally with respect to the optical probe 130.

The optical instrument or console 110 comprises a light source 111, which is adapted to generate illumination light 112. According to various embodiments described here, the light source 111 may be a laser which emits a monochromatic radiation beam. The illumination light is directed via a first optic 113 onto a first fiber end 141 of an optical fiber 140.

The console 110 further comprises a spectrometer device 116 which is optically coupled to an optical fiber 145 by means of a second optic 118. The spectrometer device 116 is used for spectrally analyzing measurement light 117, which is provided by the photonic needle 130. The spectrometer device 116 may be provided with a charged coupled device (CCD) camera 119 in order to detect the measurement light 117, which is spectrally expanded by means of at least one refractive or diffractive optical element of the spectrometer device 116.

The photonic needle 130 may comprises an elongated body having a longitudinal axis. On a side wall of the elongated body there may be provided second fiber ends, which are coupled to the optical fiber 140. The second fiber ends may be oriented in such a manner, that they provide each a lateral field of view which might be used for illuminating tissue laterally surrounding the elongated body. The photonic needle 130 may further comprises a waveguide end, which is arranged at a front end of the elongated body to provide a front field of view which is oriented substantially parallel to the longitudinal axis.

The two optical fibers 140 and 145 may be optically coupled to the second fiber ends and to the front waveguide end in various combinations. Thereby, the ends may be coupled collectively or individually with the optical fiber 140 respectively the optical fiber 145. In this respect it is pointed out that the outlets, which are optically coupled to the optical fiber 145 respectively the spectrometer device 116 represent de facto an optical inlet, because measurement light, which has been scattered by the tissue, can enter these inlet such that this measurement light can be analyzed by means of the spectrometer device 116.

According to various embodiments, the lateral fiber ends of the photonic needle 130 are assigned to the same optical fiber 140. However, it may also be possible to use one separate optical fiber for each lateral fiber end and/or for the front waveguide end. Of course, also less or more than two lateral fiber ends might be provided at the side wall of the elongated body of the photonic needle 130.

According to a first embodiment, the photonic needle 130 is positioned using image guidance in normal tissue, e.g. fat in breast tissue. To confirm that normal fat tissue is probed the characteristic spectral features of lipids at 1210 nm can be used as a guide for the eye, or by using in the console 110 or the spectrometer device 116 a real-time fat fitting model that determines amongst other parameters the amount of fat, or a trained classification model (such as principal component analysis (PCA), or partial least squares (PLS)) on fat spectroscopic measurements. Fat tissue can be easily discriminated from the rest of the tissue types for all patients. Multiple measurements may be taken to set a reference normal fat database for the patient. Then, the photonic needle 130 proceeds towards other tissue types. When the spectra fall outside a determined threshold in a PLS-DA model, e.g. PLS-DA score 3>0.5, the tissue could be suspicious. If the goal of the clinician is to target suspicious tissue he/she could decide here to take for instance a biopsy.

Figure 2:
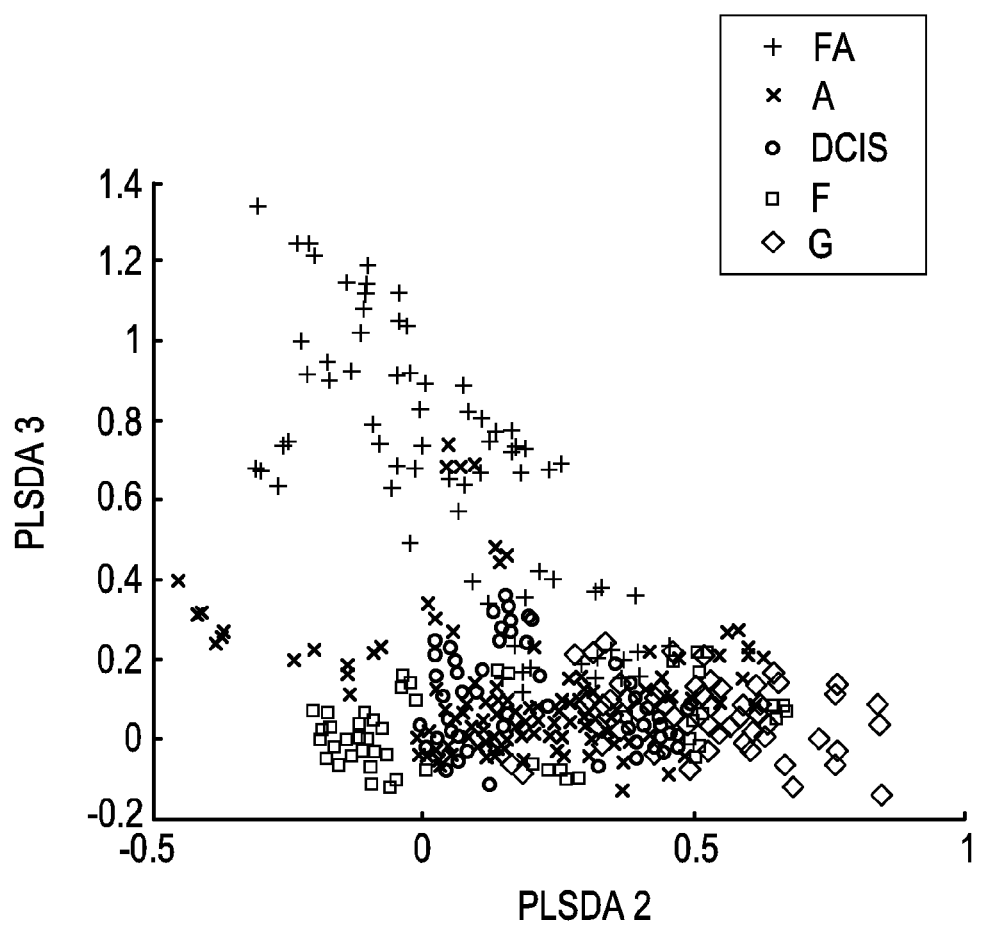
FIG. 2 shows a score plot of PLS-DA predictions with inter-patient variations.
Figure 3:
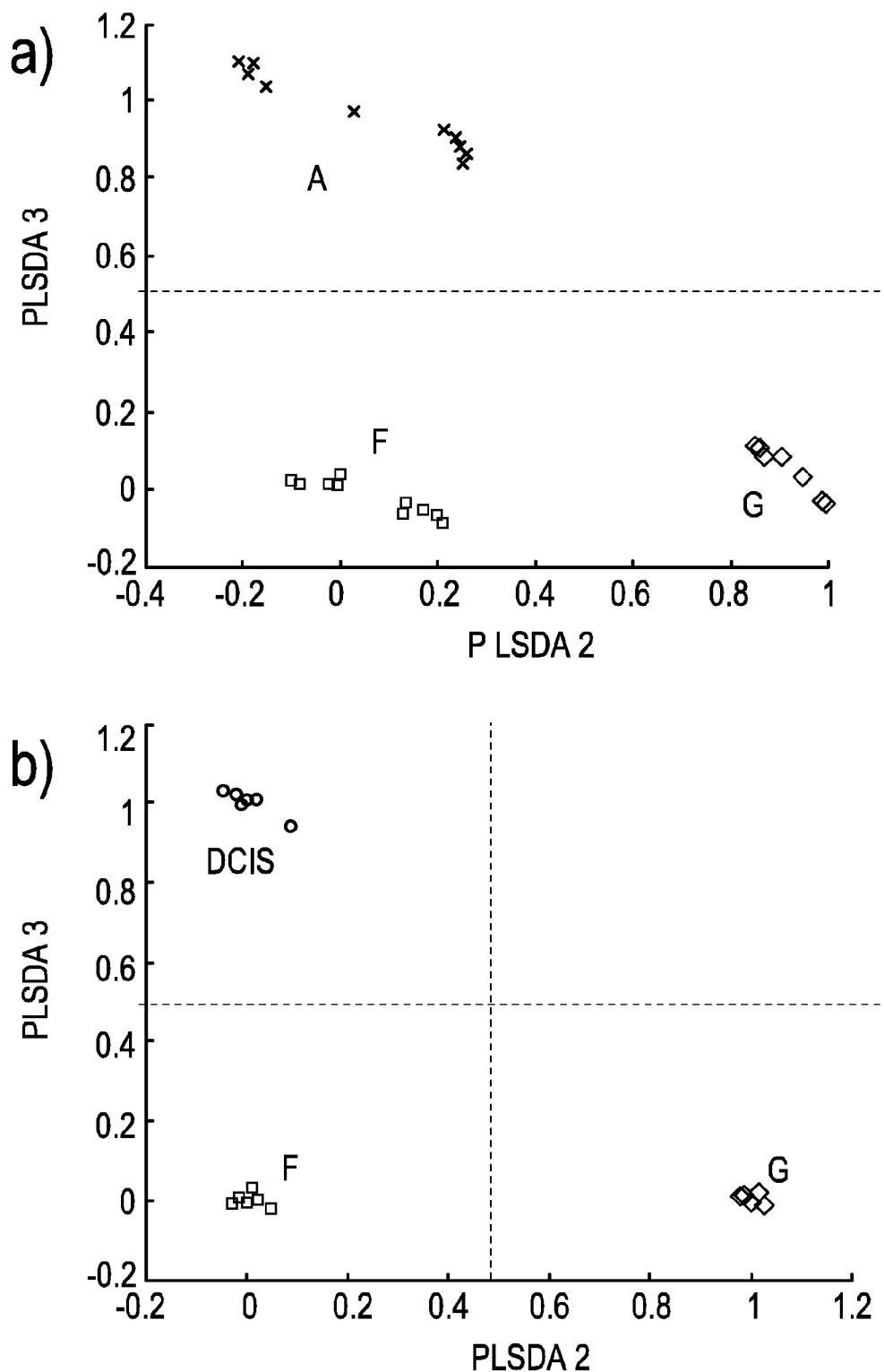
FIGS. 3a and 3b show score plots of PLS-DA predictions with intra-patient variations and threshold lines according to a first embodiment.

FIGS. 3a and 3b show examples of classification of spectroscopic data on (ex-vivo) breast tissue of individual patients. More specifically, intra-patient variation is shown in the score plots of PLS-DA predictions of breast tissue classification of two different individual patients. In FIG. 3 and the following figures, the symbols of FIG. 2 are also used to distinguish among different tissue type measurements in the diagrams. In FIG. 3a, fat (F), gland (G) and adenocarcinoma (A) tissues were measured, while in FIG. 3b, fat (F), gland (G) and ductal carcinoma in situ (DCIS) tissues were measured. As an example a simple threshold PLS-DA score 3>0.5 separates normal tissue (fat and gland) from adenocarcinoma in FIG. 3a or DCIS in FIG. 3b. It is noted that the axes in FIGS. 3a and 3b represent PLS-DA score 2. versus PLS-DA score 3. Furthermore, it is noted that the threshold is defined relative to the first tissue class, hence fat, in this case. Although the example relates to ex-vivo tissue, the invention can equally well be applied to in-vivo tissue. Thus, FIGS. 3a and 3b show intra-patient variation (and separation) of three different tissue types. According to the first embodiment, knowing the position in the scores of the first normal class that is determined on the basis of pre-knowledge, the malignant types of tissue can now be determined with respect to this first class. In individual. patients the situation shown in FIGS. 3a and 3b can occur, where three different clouds of data points appear on the basis of classification (such as PLS-DA) prediction scores. Such typical triangular shapes of data clouds can be used to differentiate normal versus malignant tissue classes. By applying a priori knowledge on the typical characteristics malignant data points can be recognized from the shape of this plot. For example different malignant tissue types show up at different positions in the score plots.

From FIGS. 3a and 3b it can also be inferred that fat and gland tissue (i.e. normal tissue) can be easily separated from adenocarcinoma and DCIS tissue (i.e. malignant tissue). A physician could in both cases decide to take biopsies from these sites. However in order to separate adenocarcinoma and DCIS more information is needed. Therefore, according to a second embodiment, the discrimination procedure of the console 110 or the spectrometer device 116 starts with a normal class. Then, it proceeds to determine a second tissue class relative to the first class, and proceeds to define a third class relative to the first and second classes. The orientation of the "triangle" defined by the three classes is then used by the console 110 or the spectrometer device 116 to finally assign to class 2 and 3 the type of malignancy, i.e. DCIS or adenocarcinoma.

Figure 4:
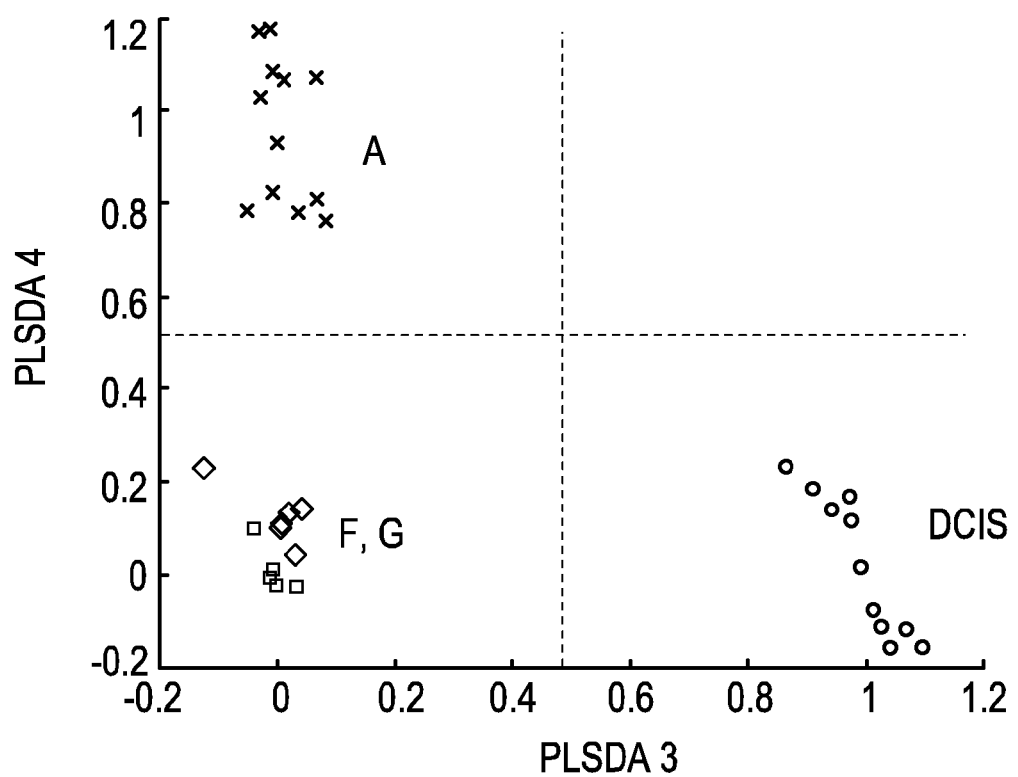
FIG. 4 shows a score plot of PLS-DA predictions with intra-patient variations and threshold lines according to a second embodiment.

FIG. 4 shows a score plot of PLS-DA predictions of breast tissue classification of an individual patient with four different tissue types (e.g. fat (F), gland (G), DICS and adenocarcinoma (A)). It is noted that the malignant tissue type classes of DCIS and adenocarcinoma are separated here in the PLS-DA score 3 versus PLS-DA score 4 plot. A first simple threshold of PLS-DA score 3>0.5 separates DCIS from the other tissue types and a second simple threshold of PLS-DA score 4>0.5 separates adenocarcinoma from the other tissue types, while PLS-DA score 3<0.5 and PLS-DA score 4<0.5 separates normal (fat and gland) from malignant (DCIS and adenocarcinoma). It is further noted that the above thresholds are defined relative to the first class of tissue which is fat in this case. In FIG. 4 the four different tissue type classes are presented in score plot axes 3 versus 4. Now, the normal tissue type classes of fat and gland are closely together and both malignant types DCIS and adenocarcinoma are separated in the two-dimensional plane of PLS-DA scores 3 and 4.

Figure 5:
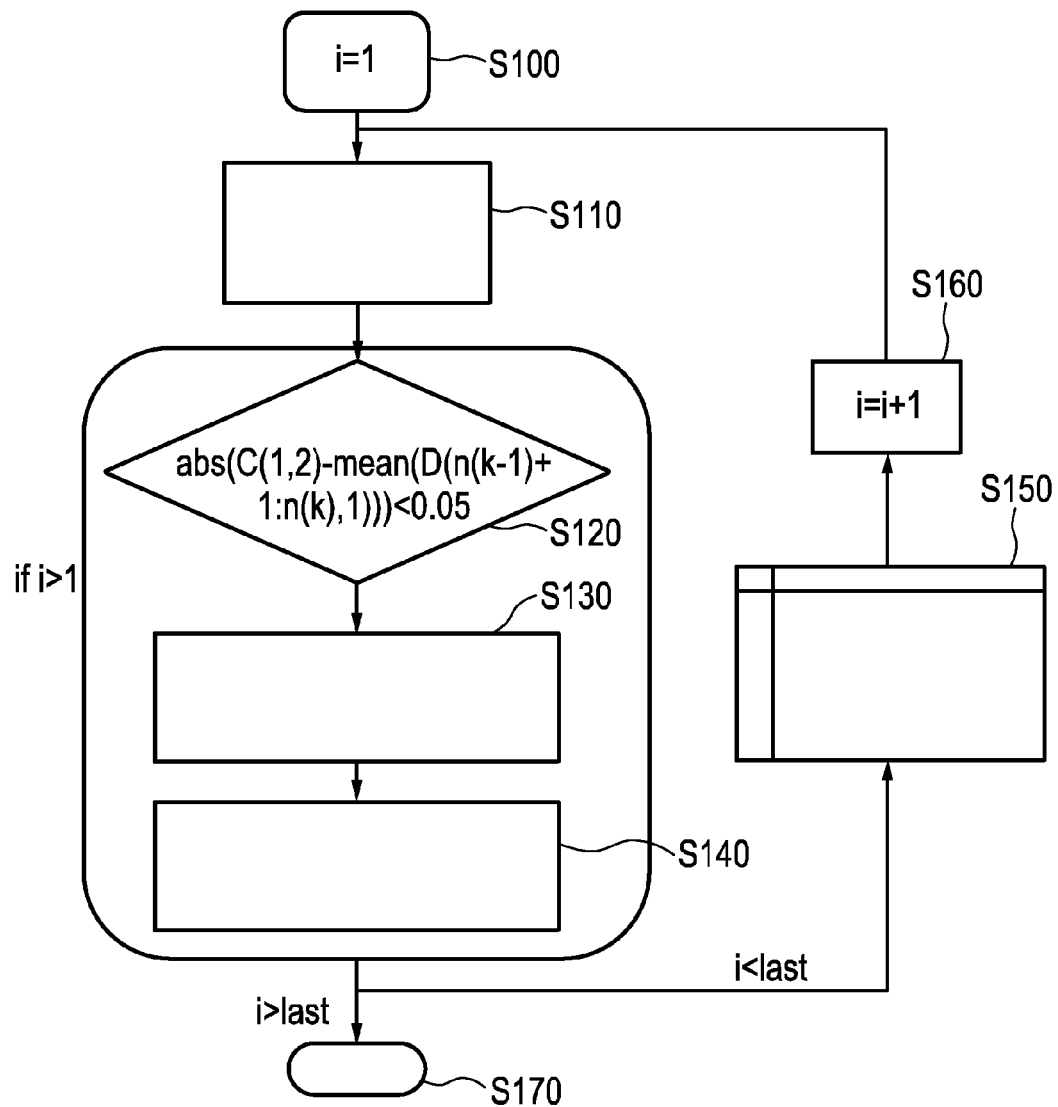
FIG. 5 shows a flow diagram of a correlation-based classification according to a third embodiment.

FIG. 5 shows a schematic flow diagram of a discrimination and classification procedure for separating normal (and/or benign) tissue from malignant tissue according to a third embodiment. The flow diagram of FIG. 5 is based on a correlation classification model where each spectrum is stored in a patient database. Here, a correlation of measured spectra with the database of individual patient spectra is used. Such a database can be build from adding subsequent measured spectra in classes based on the spectral characteristics.

According to FIG. 5, the procedure starts in step S100 with an initial setting of a running parameter i=1. Then, in step S110 a spectrum spec(i) of probed tissue is measured and read. As long as the running parameter I is larger than one and smaller than a maximum value (i.e. i>1 and i<last) the measured spectrum spec(i) is correlated in step S120 with the spectra stored in the patient database (DB). Based on a predetermined threshold (here: 0.5) of the correlation coefficient, the measured spectrum spec(i) is classified in step S130. Then, in step S140 the classification result is determined. If the running parameter i is not less than the maximum value, the measured spectrum spec(i) is stored in the database in step S150 in accordance with the classification result and the running parameter is incremented in step S160 before the procedure returns to step S110 and the next spectrum is measured. When the running parameter i has exceeded its maximum value (i>last), the procedure ends at step S170.

Figure 6:
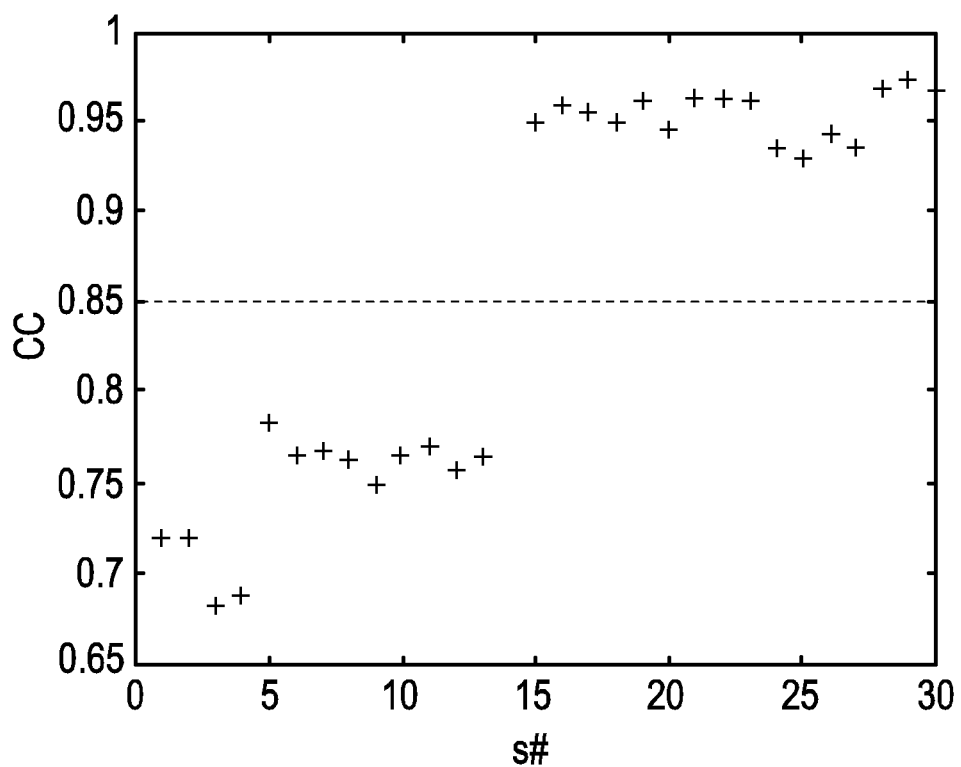
FIG. 6 shows a score plot of the correlation-based classification with intra-patient variations and a threshold line as obtained for an ex-vivo spectra after biopsy according to the third embodiment.

The practical use of this procedure is that it can start from an empty database and build an individual patient spectral database with each new spectral measurement. The actual result using this correlation approach for classification of breast tissue types is presented in FIG. 6 which shows a plot of correlation coefficients vs. spectrum number obtained from an analysis a plurality of measured spectra of breast tissue of a single patient. Here, a correlation coefficient threshold of 0.85 (dashed horizontal line in FIG. 6) can be defined to separate normal tissue (fat and gland tissue) from malignant tissue (adenocarcinoma) in this individual patient. In the example of FIG. 6, a first set of measured spectra No. 1 to 8 has been obtained from fat tissue, a second set of measured spectra No. 9 to 13 has been obtained from glandular tissue, and a third set of measured spectra No. 14 to 30 has been obtained from adenocarcinoma tissue. Thus, a single threshold can be used to separate normal tissue (fat and gland tissues) from malignant (adenocarcinoma) tissue.

Figure 7:
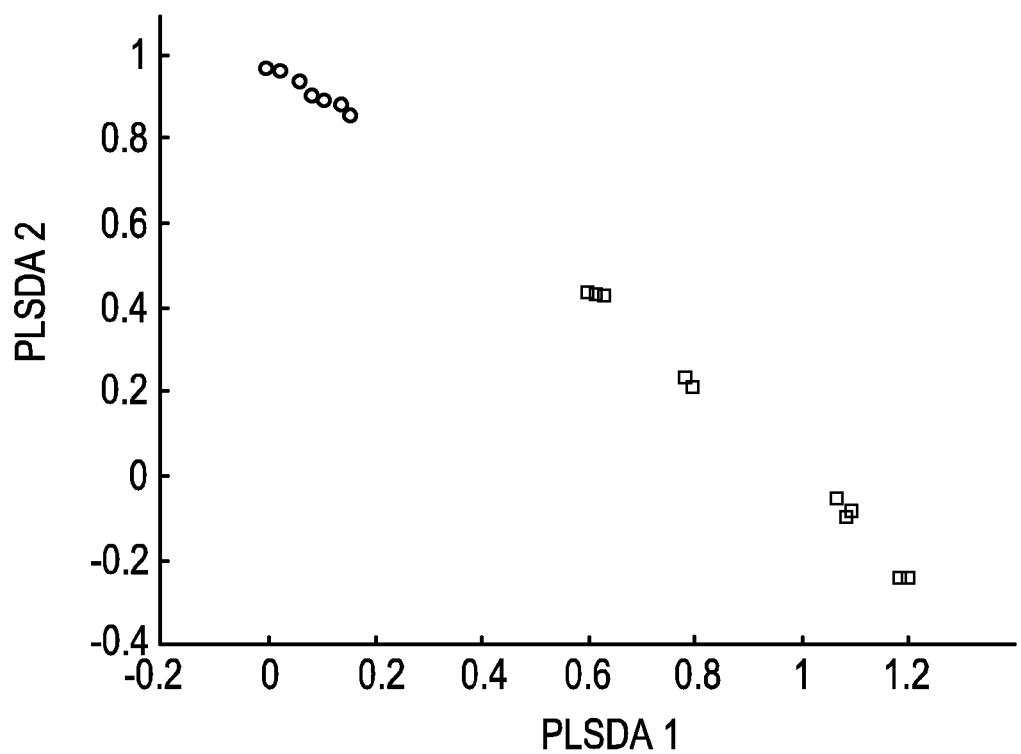
FIG. 7 shows a score plot of PLS-DA predictions with intra-patient variations and threshold lines.

FIG. 7 shows a score plot of PLS-DA predictions with intra-patient variations and threshold lines as obtained for an ex-vivo spectra after biopsy according to the third embodiment. The breast tissue spectra are classified into classes normal and benign tissue (squares) versus malignant tissue (circles) for another individual patient. A single threshold can be defined e.g. PLS-DA score 1<0.5 that classifies the spectra in Malignant type. Threshold PLS-DA score 2>0.5 does the same. The example shown here shows that a simple correlation threshold can give an indication on the type of tissue at the tip of the probe and could help to decide if a biopsy at this location is needed or not.

Figure 8:
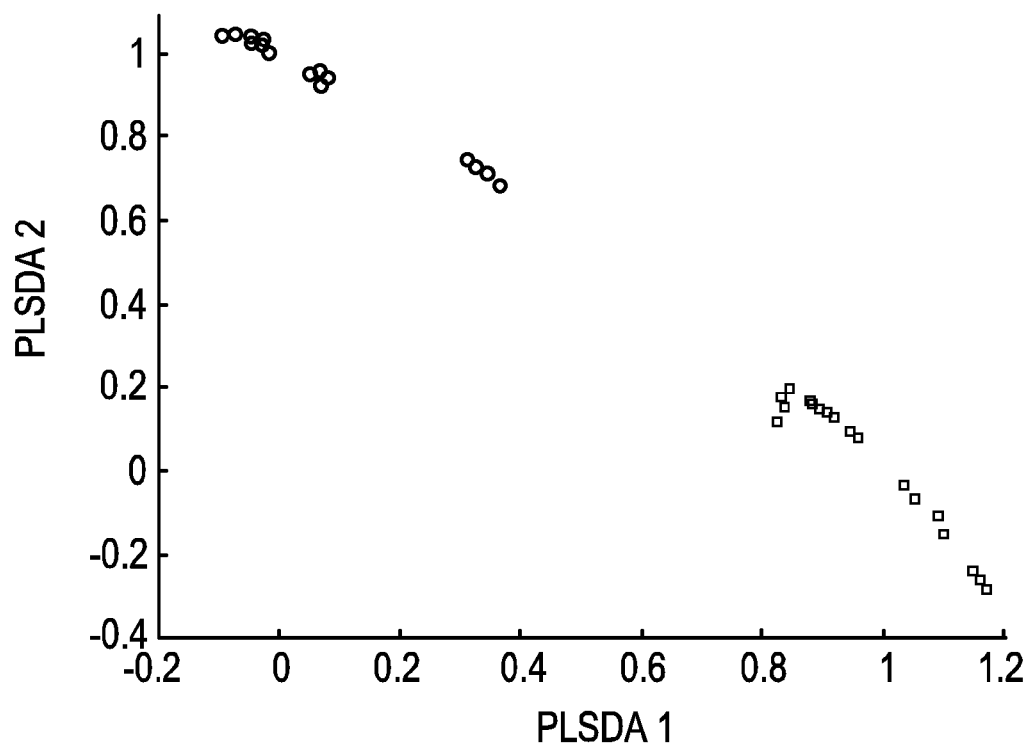
FIG. 8 shows a score plot of PLS-DA classification with intra-patient variations for another ex-vivo spectra after biopsy according to the third embodiment.

FIG. 8 shows a score plot of a PLS-DA classification with intra-patient variations for another ex-vivo spectra after biopsy according to the third embodiment. In this case, liver tissue has been examined. It can be seen that the same threshold setting also works for this liver patient in tissue type classes normal and benign (squares) vs. malignant (circles). A single threshold PLSDA score 1<0.5 classifies the spectra in malignant tissue class type. Again, the threshold PLSDA score 2>0.5 does the same.

Figure 9:
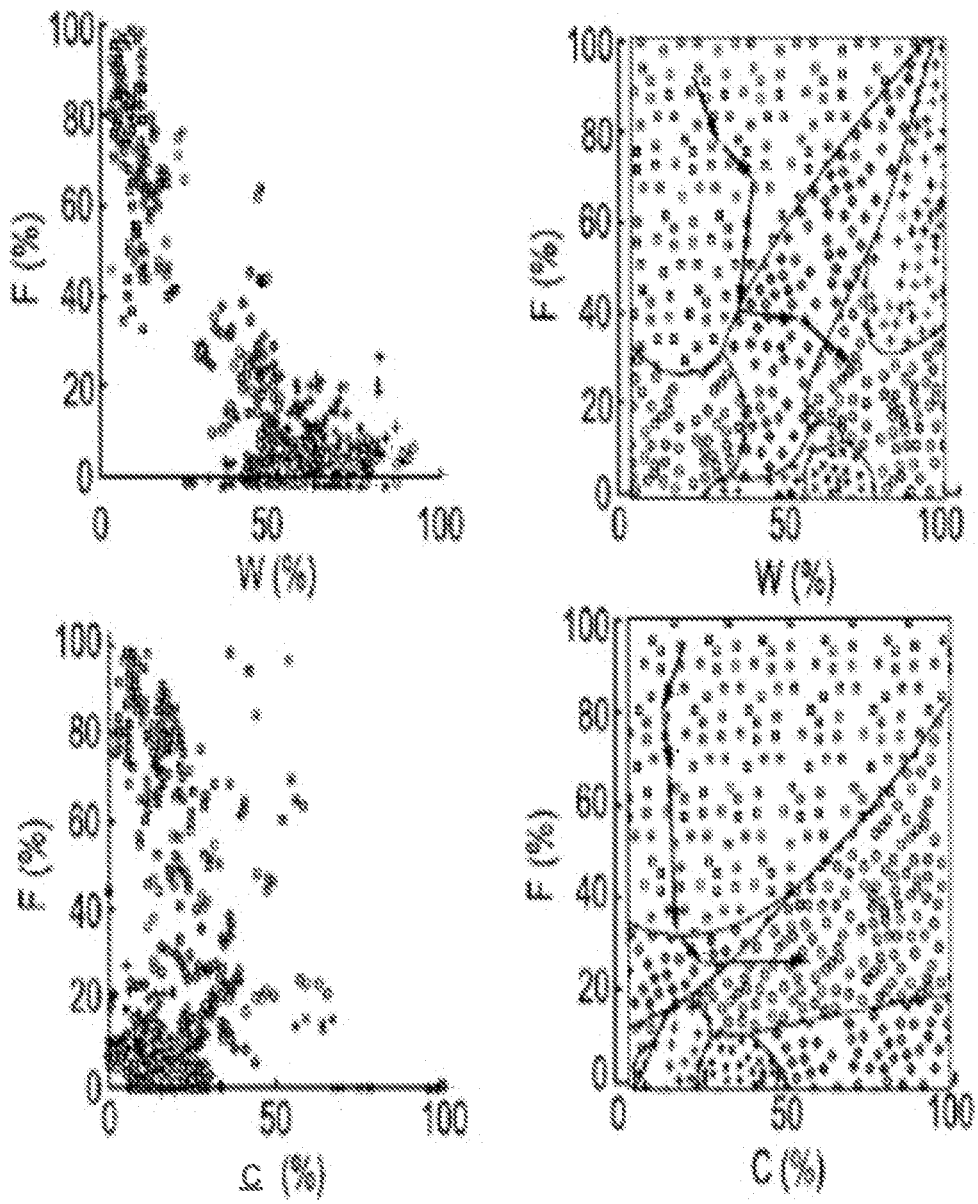
FIG. 9 shows a reference map with estimated volume fractions for classification and with measurement tracks according to a fourth embodiment.

FIG. 9 shows a reference map with estimated volume fractions for classification and with measurement tracks according to a fourth embodiment. Instead of using principal components scores to generate thresholds for classification, clinical parameters can be used, that can be derived from a model that fits the measurements and extract water (W), lipid (L) and collagen (C) fractions. FIG. 9 shows the fat vs water and fat vs collagen estimated volume fractions and the two-dimensional (2D) classification of these spaces. These 2D maps can be used by the console 110 or the spectrometer device 116 as reference maps and each measurement within a patient can be tagged on the map and tracked interactively for each new measurement acquired within a single patient as depicted in the measurement tracks of FIG. 9.

As mentioned earlier, the relative amount of fat and collagen in tissue are age-dependent. Given the fact that young patients have mainly fibroadenoma and not adenocarcinoma and DCIS, the classification can be reduced from 5 to 3 classes in a fifth embodiment.

Based on the above embodiments, experiments have been carried out, where during optical spectroscopy the tissue has been illuminated by a selected spectral band of light. Subsequent analysis of the characteristic scattering, absorption and fluorescence patterns, allows to obtain specific quantitative biochemical and morphological information from the examined tissue informative on cellular metabolic rate, vascularity, intra-vascular oxygenation and alterations in tissue morphology. Thus, optical spectroscopy allows specific differentiation between tissues by differences on molecular and morphological level and has the potential to be incorporated into optical tools for cancer diagnosis and therapy. It was hypothesized that an individualised approach in breast tissue analysis will improve discrimination accuracy for a DRS optical biopsy guidance tool.

Ex-vivo diffuse reflectance spectroscopy was performed on normal and malignant breast tissue from 24 female breast cancer patients. Tissue samples from macroscopic normal adipose tissue, glandular tissue, DCIS and invasive carcinoma were included in the optical analysis. Optical spectra were collected over a wavelength range from 500 to 1600 nm. Model based data analysis was performed on the collected tissue spectra from all patients collectively and each patient individually. Results were compared to histology analysis.

Thereby, a total of 560 spectra were collected from 115 tissue locations. Six patients were diagnosed with DCIS, 16 patients had an invasive carcinoma and 2 patients had both DCIS and an invasive carcinoma. The classification accuracy of the data from all patients divided into two groups (normal breast tissue and malignant tissue) was achieved with a sensitivity and specificity of respectively 94% and 90%. The overall classification accuracy was to 92%.

Classification of the data was also performed for each patient individually. This individualised approach yielded a 100% discrimination accuracy between normal and malignant breast tissue for 20 of the 24 patients.

As a conclusion, DRS was demonstrated to discriminate malignant tissue from normal tissue of the breast with high accuracy. 92% discriminative accuracy in an overall analysis was further enhanced to 100% for most of the included patients in an individual analysis. These results demonstrate the relevance of discrimination per-patient data towards in-vivo application and incorporation in clinical practice for minimal invasive procedures in breast tissue.

To summarize, a system and method for discrimination of malignant tissue from normal and benign tissue in a single patient on the basis of optical spectroscopic measurements has been described. Starting from spectroscopic measurements in normal tissue, reference values are obtained for the normal class. With spectroscopic measurements in other tissues data points can be assigned to new class(es) when the spectral characteristics fall outside a threshold defining the reference class. Thresholds between different classes can also be defined. Finding (the transition to) malignant tissue can be based on comparing the spectroscopic values to the classification threshold discriminating normal and benign versus malignant tissue.

While the invention has been illustrated and described in detail in the drawings and foregoing description, such illustration and description are to be considered illustrative or exemplary and not restrictive. The invention is not limited to the disclosed embodiments. There are many other ways to build up different databases for normal, benign and malignant or other tissue classes in individual patients. Standard multivariate statistical analysis methods such as principal component analysis, linear discriminant analysis, partial least squares discriminant analysis, support vector machine and others can be used for these purposes. Furthermore, other variations to the disclosed embodiment can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for obtaining at least one patient specific threshold for discrimination among different tissue types within a patient, the system comprising:
    an optical probe configured to obtain light measurements at one or more positions in tissue of a patient;
    a means for confirming said optical probe is positioned to obtain light measurements at one or more positions in patient tissue of a first tissue type; and
    a console arranged configured to:
        spectrally analyze light measurements obtained by the optical probe at said one or more positions in patient tissue of the first tissue type,
        calculate predetermined spectral characteristics for the patient tissue of the first tissue type derived from fits of the spectrally analyzed light measurements obtained by the optical probe at said one or more positions in patient tissue of the first tissue type
        define patient specific first tissue type data points in a score plot of a multivariate statistical analysis to form a patient specific first tissue type class as a first tissue type class on a basis of the calculated predetermined spectral characteristics for the patient tissue of the first tissue type,
        define a first patient specific threshold on the score plot for the first tissue type class by using (1) the calculated predetermined spectral characteristics for the patient tissue of the first tissue type as a reference tissue of the first tissue type class and (2) intra-patient a priori knowledge of the predetermined characteristics for the first tissue type and/or other tissue types relative to the first tissue type, spectrally analyze further light measurements obtained by the optical probe at another position in patient tissue, calculate the predetermined spectral characteristics for the further light measurements derived from fits of the spectrally analyzed further light measurements obtained by the optical probe at said another position in patient tissue, define data points for the further light measurements in the score plot on a basis of the calculated predetermined spectral characteristics for the further light measurements, test whether the data points for the further light measurements fall outside the first patient specific threshold in said score plot, and define a patient specific second tissue type class as a second tissue type class on the basis of the calculated predetermined spectral characteristics for the further light measurements if the data points for the further light measurements fall outside the first patient specific threshold in said score plot.

2. The system according to claim 1, wherein said predetermined spectral characteristics comprise absorption and scattering characteristics.

3. The system according to claim 1, wherein said predetermined spectral characteristics comprise fluorescence characteristics.

4. The system according to claim 1, wherein said different tissue types comprise different normal types of tissue, or normal and diseased tissue; or normal and tumor tissue, or normal tissue, benign and malignant tissue.

5. The system according to claim 1, wherein said optical probe comprises a needle, a catheter or an endoscope.

6. The system according to claim 1, wherein the console is further configured to recognize data points in said score plot as belonging to the second tissue type class based on a plot shape of said data points in said score plot.

7. The system according to claim 1, wherein the first tissue type class relates to fat or gland tissue and the second tissue type class relates to adenocarcinoma or ductal carcinoma in situ tissue.

8. The system according to claim 1, wherein the console is further configured to:
define a third tissue type class from data points in said score plot not classified in either the first or second tissue type classes, and
assign tissue types to the second and third tissue type classes based on an orientation of a triangle defined by data points of the first, second, and third tissue type classes in said score plot.

9. The system according to claim 1, wherein the console is further configured to discriminate or identify tissue types of the first and second tissue type classes based on a known correlation between measured spectra and a database of individual patient spectra.

10. The system according to claim 1, wherein the console is further configured to:
generate a reference map in a space defined by at least two selected from the group consisting of extracted water, lipid, and collage fractions,
classify the space based on the tissue type, and
tag the reference map with data point representing the spectrally analyzed light measurements.

11. A method for obtaining at least one threshold for discrimination among different tissue types, the method comprising:
positioning an optical probe at one or more positions in patient tissue of a first tissue type under guidance of a position confirmation means;
obtaining light measurements at said one or more positions in patient tissue of said first tissue type with the optical probe;
spectrally analyzing the light measurements obtained by the optical probe at said one or more positions in patient tissue of the first tissue type;
calculating predetermined spectral characteristics for the patient tissue of the first tissue type derived from fits of the spectrally analyzed light measurements obtained by the optical probe at said one or more positions in patient tissue of the first tissue type;
defining patient specific first tissue type data points in a score plot of multivariate statistical analysis to form a patient specific first tissue type class as a first tissue type class on a basis of the calculated predetermined spectral characteristics for the patient tissue of the first tissue type;
defining a first patient specific threshold on the score plot for the first tissue type class by using (1) the calculated predetermined spectral characteristics for the patient tissue of the first tissue type as a reference tissue of the first tissue type class and (2) intra-patient a priori knowledge of the predetermined characteristics for the first tissue type and/or other tissue types relative to the first tissue type;
positioning the optical probe at further positions in the tissue;
obtaining further light measurements at said further positions in the tissue with the optical probe;
spectrally analyzing said further light measurements;
calculating the predetermined spectral characteristics for the further light measurements derived from fits of the spectrally analyzed further light measurements;
defining data points for the further light measurements in the score plot on a basis of the calculated predetermined spectral characteristics for the further light measurements;
testing whether the data points for the further light measurements fall outside the first patient specific threshold in said score plot; and
defining a patient specific second tissue type class as a second tissue type class on the basis of the calculated predetermined spectral characteristics for the further light measurements if the data points for the further light measurements fall outside the first patient specific threshold in said score plot.

12. The method according to claim 11, wherein said predetermined spectral characteristics comprise absorption and scattering characteristics.

13. The method according to claim 11, wherein said predetermined spectral characteristics comprise fluorescence characteristics.

14. The method according to claim 11, wherein said different tissue types comprise different normal types of tissue, or normal and diseased tissue, or normal and tumor tissue, or normal tissue, benign and malignant tissue.

15. The method according to claim 11, wherein said optical probe comprises a nee a catheter or an endoscope.

16. The method according to claim 11, further comprising recognizing data points in said score plot as belonging to the second tissue type class based on a plot shape of said data points in said score plot.

17. The method according to claim 11, wherein the first tissue type class relates to fat or gland tissue and the second tissue type class relates to adenocarcinoma or ductal carcinoma in situ tissue.

18. The method according to claim 11, further comprising:
   defining a third tissue type class from data points in said score plot not classified in either the first or second tissue type classes; and
   assigning tissue types to the second and third tissue type classes based on an orientation of a triangle defined by data points of the first, second, and third tissue type classes in said score plot.

19. The method according to claim 11, further comprising discriminating or identifying tissue types of the first and second tissue type classes based on a known correlation between measurement spectra and a database of individual patient spectra.

20. The method according to claim 11, further comprising:
   generating a reference map in a space defined by at least two selected from the group consisting of extracted water, lipid, and collagen fractions;
   classifying the space based on the tissue types; and
   tagging the reference map with data points representing the spectrally analyzed light measurements.

* * * * *